US00PP19872P2

(12) United States Plant Patent
Carruth

(10) Patent No.: US PP19,872 P2
(45) Date of Patent: Mar. 31, 2009

(54) HYBRID TEA ROSE PLANT NAMED 'WEKMOOMAR'

(50) Latin Name: *Rosa hybrida*
Varietal Denomination: WEKmoomar

(75) Inventor: Thomas F. Carruth, Altadena, CA (US)

(73) Assignee: Weeks Wholesale Rose Grower, Inc., Pomona, CA (US)

( * ) Notice: Subject to any disclaimer, the term of this patent is extended or adjusted under 35 U.S.C. 154(b) by 0 days.

(21) Appl. No.: 11/986,368

(22) Filed: Nov. 20, 2007

(51) Int. Cl.
*A01H 5/00* (2006.01)

(52) U.S. Cl. ..... Plt./137

(58) Field of Classification Search ..... Plt./137
See application file for complete search history.

*Primary Examiner*—Kent L Bell
(74) *Attorney, Agent, or Firm*—Christie, Parker & Hale, LLP.

(57) ABSTRACT

A new variety of Hybrid Tea rose suitable for garden decoration, having flowers of warm pink with a cream reverse coloration.

1 Drawing Sheet

Classification: The present invention relates to a new *Rosa hybrida* plant.

Variety denomination: The new plant has the varietal denomination 'WEKmoomar'.

BACKGROUND OF THE INVENTION

This invention relates to a new and distinct variety of Hybrid Tea Rose. It has as its seed parent the variety known as 'WEKcryland' (U.S. Plant Pat. No. 11,384) and as its pollen parent the variety known as 'WEKsunspat' (U.S. Plant Pat. No. 14,398).

SUMMARY OF THE INVENTION

Among the features which distinguish the new variety from other presently available and commercial rose cultivars known to the inventor are the following combinations of characteristics: its rough peduncle with some small prickles, its wash of green along the central vein of the outermost petals, its unusual yellow green style color and its numerous large prickles on major stems, branches and new shoots. The plant has an upright growing habit, suitable for outdoor garden decoration.

Asexual reproduction of the new variety by budding as performed in Kem County and Pomona, Calif., shows that the foregoing and other distinguishing characteristics come true to form and are established and transmitted through succeeding asexual propagations. 'WEKmoomar' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, 'WEKcryland' by the following combination of characteristics: whereas 'WEKmoomar' bears double flowers (about 26 to 33 petals) of warm pink with a cream reverse coloration, 'WEKcryland' bears double flowers with significantly heavier petalage (about 34 to 42 petals) of white coloration with a very fine pink edging. The new variety has an upright growing habit (about 52 to about 66 cm. spread at the widest point), whereas the seed parent has a significantly more spreading growing habit (about 80 to about 100 cm. spread at the widest point).

The new variety may be distinguished from its pollen parent, 'WEKsunspat' by the following combination of characteristics: whereas 'WEKmoomar' bears flowers of warm pink with a cream reverse coloration, 'WEKsunspat' bears flowers of soft apricot washed with green coloration. The new variety has an upright medium height growing habit (about 120 to about 140 cm. in height and about 52 to about 66 cm. spread at the widest point), whereas the pollen parent has a somewhat upright significantly taller and more spreading growing habit (about 160 to about 200 cm. in height and about 88 to about 110 cm. spread at the widest point).

COMPARISON WITH THE CLOSEST COMMERCIALLY AVAILABLE CULTIVAR

The closest commercially available cultivar to the new variety is the seed parent 'WEKcryland'.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of November. Phenotypic expression may vary with environmental, cultural and climatic conditions, as well as differences in conditions of light and soil.

FLOWER

The new variety usually bears its flowers singly. Flowers are borne on strong somewhat short to medium length stems (about 25 to about 80 cm.). Outdoors, the plant blooms abundantly and nearly continuously during the growing season. The flowers have a moderate tea to somewhat spicy fragrance.

BUD

The peduncle is about 3.2 to about 6.4 cm. in length, of moderately heavy caliper (about 0.3 to about 0.5 cm. in diameter), and usually erect. It is rough, with few stipitate glands, many hairs and some small prickles. Peduncle color is between 146B and 137D sometimes lightly suffused, especially on the side exposed to the sun, with between 187A and 183A.

Before the calyx breaks, the bud is about 1.5 to about 2.1 cm. in diameter at the widest point, about 2.0 to about 2.5 cm. in length, and moderately ovoid to somewhat pointed in shape. The surface of the bud bears some very long foliaceous appendages and few hairs, usually with slender entire foliaceous parts extending beyond the tip of the bud about ¼ more of its length. Bud color is between 137B and 137A sometimes lightly suffused, especially on the side exposed to the sun, with between 187A and 183A.

The sepals are about 2.8 to about 4.2 cm. in length and about 0.8 to about 1.1 cm. in width at the widest point. The outer surface color of the sepal is between 137B and 137A sometimes lightly suffused, especially on the side exposed to the sun, with between 187A and 183A. The inner surface color of the sepal is between 137B and 138B and covered with fine wooly tomentum; sepal margins are lined with some stipitate glands and hairs.

The receptacle of the flower is of somewhat short length (about 0.4 to about 0.6 cm.) and moderately thin in caliper (about 0.8 to about 1.1 cm. in diameter). The receptacle is somewhat urn-shaped in form with a flat top. Its surface is very smooth with few hairs and with thick fleshy walls. The receptacle color is between 144A and 138A.

As the petals open (after the calyx breaks), the bud is about 2.4 to about 2.8 cm. in diameter at the widest point, about 3.0 to about 4.0 cm. in length, and in moderately ovoid form. The color of the under surfaces of the newly opened petals is between 4D and 158C often washed along the central vein of the outermost petals with between 145A and 145B and lightly blushed mostly on the edge of the petals with between 61B and 61C. There is no visible change in coloration at the point where the petal attaches. On the upper surfaces of the newly opened petals, the color at the base of the petal is between 1D and 2D that gradually suffuses toward the center of the petal to near 55C, usually moderately blushed toward the petal edge with between 63B and 61C. There is no visible change in coloration at the point where the petal attaches.

BLOOM

When fully open, the bloom ranges from about 10.5 to about 13.9 cm. in diameter. Petalage is double with about 26 to 33 petals and about 2 to 6 petaloids irregularly arranged. When partially open, the bloom form is somewhat high centered to moderately cupped, and the petals are moderately tightly spiraled to cupped with petal edges slightly reflexed outward. When fully open, the bloom form is more cupped, and the petals are loosely cupped with petal edges moderately reflexed outward.

PETALS

The substance of the petals is moderately heavy and somewhat thick, with upper surfaces moderately satiny to somewhat shiny and under surfaces moderately shiny. The petals are about 4.8 to about 6.9 cm. in length and about 4.1 to about 7.2 cm. in width at the widest point. Petal margins are entire.

The outer petals are rounded in shape with rounded apices.

The inner petals are broadly obovate in shape with rounded apices and sometimes slightly notched with one notch.

Petaloids are about 3.1 to about 5.0 cm. in length and about 2.7 to about 4.6 cm. in width at the widest point. Petaloids are irregularly shaped moderately rounded to somewhat obovate with rounded apices.

NEWLY OPENED FLOWER

On the under surfaces of the outer petals, the color at the base of the petal is between 155A and lighter than 2D gradually suffusing on the petal to between 155A and 155C, sometimes lightly blushed toward the petal edge with between 64C and 61C. There is no visible change in coloration at the point where the petal attaches. On the upper surfaces of the outer petals, the color at the base of the petal is lighter than between 1D and 2D gradually suffusing toward the center of the petal to between 62D and lighter than 55D, usually lightly blushed toward the petal edge with between 64C and 61C. There is no visible change in coloration at the point where the petal attaches.

On the under surfaces of the intermediate and inner petals, the color at the base of the petal is between 155A and lighter than 2D gradually suffusing on the petal to between 155A and 158D, sometimes lightly blushed toward the petal edge with between 64C and 61C. On the upper surfaces of the intermediate and inner petals, the color at the base of the petal is lighter than between 1D and 2D gradually suffusing toward the center of the petal to between 63D and 62B, usually moderately blushed toward the petal edge with between 64C and 55A.

The under and upper surface color of the petaloids are similar in coloration to the upper and under surfaces of the intermediate and inner petals.

The general tonality of the newly opened flower is lighter than between 1D and 2D at the base gradually suffusing toward the center of the petal to between 63D and 62B, usually moderately blushed toward the petal edge with between 64C and 55A.

THREE-DAY-OLD FLOWER

On the under surfaces of the outer, intermediate and inner petals, the color at the base of the petal is between 155A and lighter than 4D gradually suffusing on the petal to between 155D and 155C, sometimes lightly blushed toward the petal edge with between 64C and 61C. There is no visible change in coloration at the point where the petal attaches. On the upper surfaces of the outer, intermediate and inner petals, the color at the base of the petal is lighter than between 2D and 4D gradually suffusing toward the center of the petal to between 62D and 65D, sometimes lightly blushed toward the petal edge with between 64C and 61C. There is no visible change in coloration at the point where the petal attaches.

The under and upper surface color of the petaloids are similar in coloration to the upper and under surfaces of the intermediate and inner petals.

The general tonality of the three-day-old flower is lighter than between 2D and 4D at the base gradually suffusing toward the center of the petal to between 62D and 65D, sometimes lightly blushed toward the petal edge with between 64C and 61C.

On the spent bloom, the petals usually drop off cleanly.

In November in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 165) and are arranged regularly about the pistils; a few are mixed with petaloids. The filaments are of medium to somewhat long length (about 0.7 to about 1.4 cm.) most with anthers. Filaments are between 4D and 2D in color sometimes lightly suffused with near 53C. The anthers are moderately small for the class and all open approximately at the same time. Anther color when immature is near 19A on the external part and near 18C on the internal part. Anther color at maturity is near 200A on the external part and near 165B on the internal part. Pollen is moderately abundant and near 18C in color.

FEMALE REPRODUCTIVE ORGANS

Pistils vary in number (average about 105). The styles are somewhat uneven, moderately long in length (about 0.5 to about 0.8 cm.), average in caliper, and moderately separated. Stigma color is between 8A and 6C. Style color is near 145B at the base gradually suffusing to 145D and usually moderately blushed near the top with near 53C. Ovaries are usually all enclosed in the calyx.

Hips are moderately long in length (about 2.8 to about 3.2 cm.), globular in form, and between 26A and 25A in color when ripe. The hip surface is very smooth with thick fleshy walls. The sepals are somewhat permanent, and usually straight in shape.

The seeds are irregularly rounded, smooth in texture, approximately 4 to about 12 per hip, about 0.6 to about 0.8 cm. in diameter at the widest point and between 162B and 161B in color.

FOLIAGE

The compound leaves are usually comprised of three to seven leaflets and are borne abundantly. The seven-leaflet leaves are about 10.0 to about 16.5 cm. in length and about 8.4 to about 13.3 cm. in width at the widest point, moderately leathery to somewhat crisp in texture, and glossy in finish. The terminal leaflets are about 4.6 to about 7.6 cm. in length and about 2.7 to about 5.2 cm. in width at the widest point, shaped ovate with acute to somewhat acuminate apices and rounded bases. Their margins are usually simply serrate.

The upper surface color of the mature leaf is between 137A and 137B. The under surface color of the mature leaf is between 147B and 139B. The upper surface color of the young leaf is between 137C and 138A, usually moderately suffused with between 187B and 183B. The under surface color of the young leaf is between 138B and 137C, usually heavily suffused with between 187B and 183B.

The rachis is average to somewhat heavy in caliper and rough. The upper side is shallowly grooved with few hairs and some stipitate glands on the edges of the grooves. The under side of the rachis is rough with few stipitate glands and some small prickles. The rachis color is near 146B on the under side and near 146A on the upper side sometimes moderately suffused on the young leaves with between 187A and 187B.

The stipules are about 1.4 to about 2.2 cm. in length and moderately wide (about 0.5 to about 1.0 cm.) with short straight points that usually turn out at an angle of more than 45 degrees. The stipule color is between 137B and 137A sometimes lightly suffused on the young leaves with between 187C and 183C.

The petiole is average to somewhat heavy in caliper and rough. The upper side is shallowly grooved with few hairs and some stipitate glands on the edges of the grooves. The under side of the petiole is rough with few stipitate glands and some small prickles. The petiole is about 0.1 to about 0.8 cm. in length and about 0.1 to about 0.2 cm in diameter at the widest point. The petiole color is near 146B on the under side and near 146A on the upper side sometimes moderately suffused on the young leaves with between 187A and 187B.

The plant displays an average degree of resistance to powdery mildew and rust as compared to other commercial varieties grown under comparable conditions in Pomona, Calif. The plant's winter hardiness and drought/heat tolerance are yet to be determined.

GROWTH

The plant has an upright medium height growing habit (about 120 to about 140 cm. in height and about 52 to about 66 cm. spread at the widest point), with full branching. It displays moderately vigorous growth and the canes are of medium to somewhat heavy caliper for the class.

The color of the major stems is between 147B and 146A. They bear numerous large prickles that are about 0.6 to about 1.0 cm. in length. The large prickles are slightly angled downward to somewhat hooked with a somewhat long moderately narrow oval base; prickle color is between 165B and 164A. The major stem bears few small prickles of similar shape and coloration.

The color of the branches is between 146A and 137B. They bear numerous large prickles which are of similar size and shape to the large prickles on the major stems; prickle color is between 152B and 152A sometimes lightly suffused with between 187C and 187D. The branches bear few small prickles of similar shape and coloration.

The color of the new shoots is between 146A and 137B sometimes moderately suffused with between 187B and 183B. They bear numerous large prickles which are of similar size and shape to the large prickles on the major stems; prickle color is between 146B and 146C usually heavily suffused with between 187B and 187C. The shoots bear few small prickles of similar shape and coloration.

I claim:

1. A new and distinct Hybrid Tea rose plant of the variety substantially as described and illustrated herein.

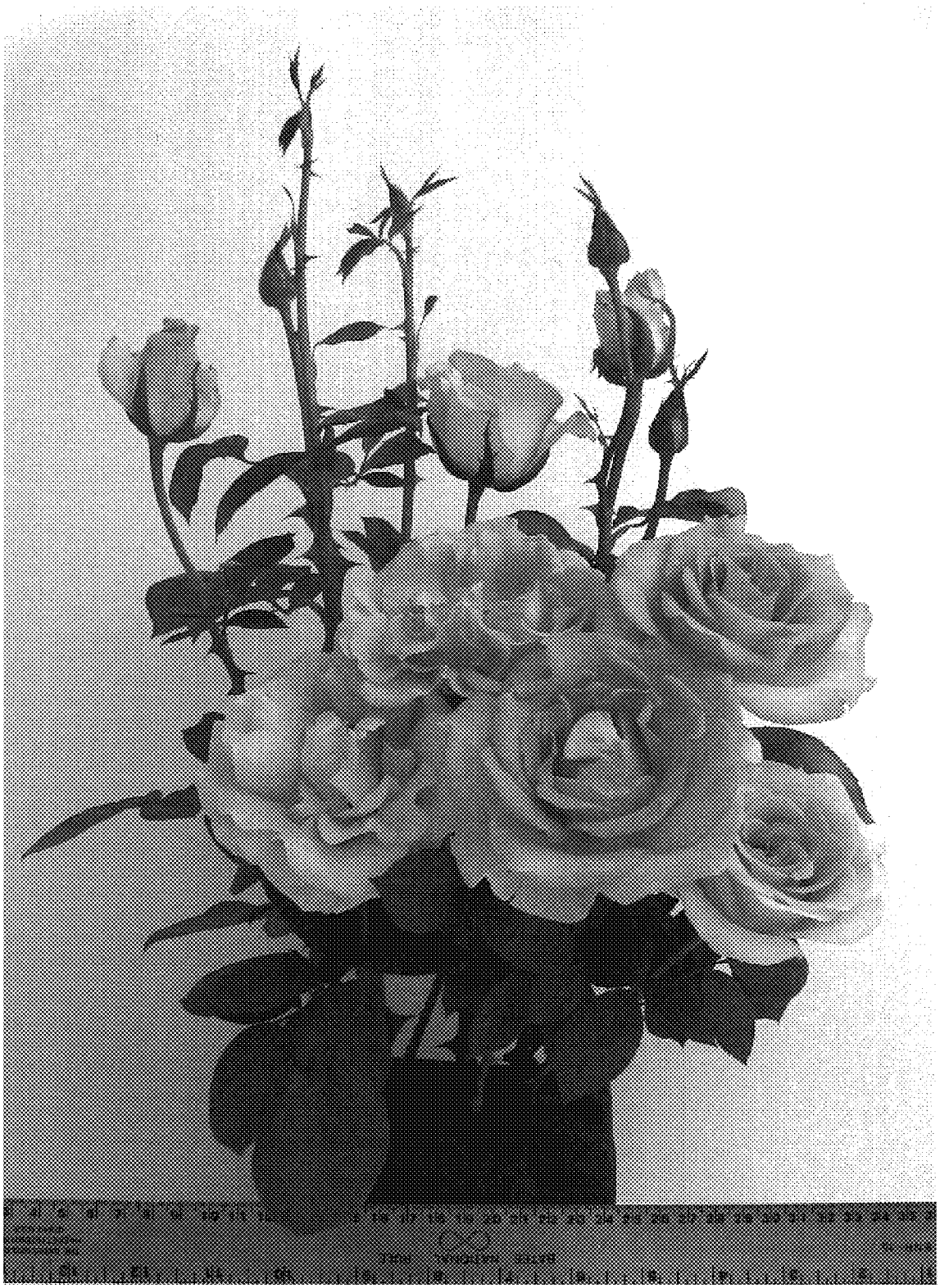

* * * * *